(12) United States Patent
Cronin et al.

(10) Patent No.: US 10,405,922 B2
(45) Date of Patent: *Sep. 10, 2019

(54) MEDICAL DEVICES AND PUMPS THEREFOR

(71) Applicant: AngioDynamics, Inc., Latham, NY (US)

(72) Inventors: Nigel Cronin, Somerset (GB); Philip Radford, Hampshire (GB)

(73) Assignee: AngioDynamics, Inc., Latham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/495,155

(22) Filed: Jul. 5, 2017

(65) Prior Publication Data

US 2018/0055566 A1 Mar. 1, 2018

Related U.S. Application Data

(63) Continuation of application No. 13/500,378, filed as application No. PCT/GB2010/051625 on Sep. 29, 2010, now Pat. No. 9,757,197.

(51) Int. Cl.
*A61B 18/18* (2006.01)
*A61M 3/02* (2006.01)
*A61B 18/00* (2006.01)

(52) U.S. Cl.
CPC ....... *A61B 18/1815* (2013.01); *A61M 3/0258* (2013.01); *A61B 2018/00023* (2013.01); *A61B 2018/1861* (2013.01); *A61M 2205/051* (2013.01); *A61M 2205/106* (2013.01); *A61M 2205/3606* (2013.01)

(58) Field of Classification Search
CPC .......................... A61M 3/0258; A61M 3/0254
See application file for complete search history.

(56) References Cited

U.S. PATENT DOCUMENTS

2005/0015081 A1* 1/2005 Turovskiy .............. A61B 18/18
606/33
2007/0203551 A1* 8/2007 Cronin ................... A61B 18/18
607/101

* cited by examiner

*Primary Examiner* — Joseph M Dietrich
(74) *Attorney, Agent, or Firm* — Peter Flora, Esq.

(57) ABSTRACT

A microwave applicator device comprising a probe (11) for ablating the body of a human or animal, a cooling passage (20,21) extending through the probe (11) and arranged to carry a cooling fluid, a pump (71) for pumping the fluid through the probe (11), and an elongate flexible duct (104) extending between the pump (71) and one end of the cooling passage (20,21), the pump comprising a pump body (73) including a motor (120) and a pump head (72) detachably mounted to the pump body (73), the pump head (72) comprising a first port (86) connected to a proximal end of the elongate flow duct (104), a second port (85) and fluid propulsion means (84,92) for creating a flow of fluid between the ports (85,86) and along the elongate flow duct 104 upon energization of the motor (120), the pump head (72) being arranged to sealingly contain the fluid. The pump head (72), the elongate flexible duct (104) and the probe (11) form a replaceable assembly that can be detached from the pump body (73) and discarded following use.

11 Claims, 5 Drawing Sheets

MEDICAL DEVICES AND PUMPS THEREFOR

This invention relates to medical devices and to pumps which are more particularly but not solely intended for use therewith.

It is well known to ablate body tissue using a microwave applicator which heats and destroys the surrounding tissue. One use of such an applicator is in the non-invasive treatment of cancer in an internal body organ such as the liver. GB2415630 discloses an applicator of the above-mentioned type comprising a probe having a thin elongate shaft which can be inserted into the patient for treatment. The proximal end of the probe comprises a handle which is connected to an external microwave generator by an elongate flexible cable. A thin elongate microwave transmission line extends inside the probe from the handle to a radiating tip or antenna disposed at or adjacent the distal end of the probe. In use, the microwave field radiated from the tip heats and ablates the surrounding tissue in a localised area.

A disadvantage of the above-mentioned applicator is that the probe can heat up for a variety of reasons. Firstly, power losses can occur in the transmission line extending along the probe to the tip, which power losses heat the transmission line and the surrounding parts of the probe. Secondly, the radiated microwave energy can heat the probe. Thirdly, the heat from the ablation can be conducted back along the probe. Such heating of the probe is undesirable, since it can burn the patient's skin at the point of entry of the probe or it can burn other parts of the patient's body adjacent the shaft of the probe: for this reason UK government regulations specify that no external part of any medical apparatus should exceed 48° in temperature.

In order to overcome the above-mentioned problems, it is known to pass a liquid, such as a saline solution, along the probe of the applicator so as to cool the probe. One such applicator is disclosed in our co-pending International Patent Application No. PCT/GB2009/050113 filed 5 Feb. 2009, the contents of which are incorporated herein by reference, and comprises a probe having a pair of flow channels extending longitudinally along its shaft parallel to the transmission line, the channels being interconnected at the distal end of the shaft adjacent the radiating tip. In use, cooling fluid can be pumped through the probe to its distal end along one flow channel and then returned along another flow channel. A pair of flexible ducts extend from a handle of the probe and respectively allow the fluid flow into and out of the channels.

It will be appreciated that the flow channels have a very small diameter and hence and object of the present invention is to provide a pump which can create a sustained and reliable fluid flow through these channels that sufficiently cools the shaft of the probe.

Microwave applicator probes are generally single-use disposable items due to the fact that they cannot be reliably cleaned and sterilised following insertion into the human body. Also, since there is a risk that fluid flowing through the probe inside the body could become contaminated, it will be appreciated that both the fluid and the ducts carrying the fluid into and out of the probe need to be discarded following use. A problem with this is that the fluid also comes into contact with the pump and thus there is a risk that the fluid will contaminate the pump either directly or by virtue of the fact that there is a direct path for contaminants to travel back to the pump along the duct which connects it to the probe. Whilst pumps are difficult to clean and sterilise, they are too expensive to be discarded after each use. Accordingly, another object of the present invention is to provide a pump which overcomes this problem.

We have now devised a medical device which meets the above needs and objectives and which can be used in the treatment, therapy or diagnosis of the human or animal body.

In accordance with the present invention, as seen from a first aspect, there is provided a medical device comprising a distal head portion for contacting the body of a human or animal, a cooling passage extending through the head portion and arranged to carry a fluid for cooling the head, a pump for pumping said fluid through the head portion, and an elongate flexible duct extending between the pump and one end of the cooling passage, said pump comprising a pump body including a motor and a pump head detachably mounted to the pump body, the pump head comprising a first port connected to a proximal end of said elongate flow duct, a second port and fluid propulsion means for creating a flow of said fluid between said ports and along said elongate flow duct upon energisation of said motor, said pump head being arranged to sealingly contain said fluid, wherein the pump head, the elongate flexible duct and the head portion form replaceable assembly that can be detached from the pump body following use.

It will be appreciated that any risk of contamination is avoided because the pump head, the elongate flexible duct and the head portion are all provided as a single and preferably sterile assembly which can be discarded following use. Since only the head of the pump is replaced, the replacement cost is reduced and indeed the pump head can be formed as a relatively low cost item. The pump head sealingly contains the fluid and thus the fluid does not come into contact with any unsterile parts and also cannot contaminate any parts of the device other than the replaceable assembly. Since, all of the parts which come into contact with the fluid are discarded, the need for cleaning and sterilisation is avoided.

Preferably the assembly comprises a further elongate flexible duct having a distal end extending from the other end of the cooling passage of the head portion: this further elongate flexible duct carries fluid in the opposite direction to the aforementioned elongate flexible duct and, in a preferred embodiment, is arranged for connecting to a fluid drain.

Preferably said further elongate flexible duct forms part of the disposable assembly.

Preferably an electrical cable extends to said head portion of the device, the cable preferably also forming part of said replaceable assembly.

Preferably the pump comprises a pump housing, said cable extending from said pump housing preferably being connected thereto by means of a connector provided on the pump housing.

Preferably a further cable extends from the pump housing to a main unit of the device, means being provided in said pump housing for connecting said further cable to the aforementioned cable which extends to said head portion of the device. In this way the main unit can be positioned at a remote location and the head portion is then simply electrically connected thereto by connecting it to the pump housing, which can be located adjacent the human or animal.

Preferably, the head portion comprises a microwave antenna for performing ablation of the human or animal body, the main unit comprising a magnetron or other source of microwave radiation.

Preferably the cable is also arranged to be cooled by said fluid as it flows along a said elongate flexible duct. The cable preferably forms a wall of said elongate flexible duct, the duct preferably defining a cooling jacket which surrounds the cable.

Preferably the cable is cooled by said fluid as it flows along said further elongate flexible duct.

Preferably, said further elongate flexible duct comprises a first portion having a distal end connected to said head portion of the device and a proximal end connected a first port of a manifold, the first portion of said further elongate flexible duct being arranged to cool said cable, said further elongate flexible duct further comprising a second portion which extends from a second port of the manifold, the manifold having a third port for entry of the cable, the manifold being sealed and arranged such that the cable entering the manifold extends inside said first portion of said further elongate flexible duct and is cooled by fluid flowing via the first and second ports of the manifold, said manifold forming part of the disposable assembly.

Preferably the manifold comprises a further port to allow another cable to extend inside said first portion of said further elongate flexible duct: this further cable may carry signals from a sensor disposed in said head portion of the device.

Preferably the manifold is disposed adjacent the pump

Preferably the assembly comprises another elongate flexible duct connected to said second port of the pump head: preferably the distal end of this other elongate flexible duct is arranged for connecting to a fluid source, such as a bag containing saline.

Preferably said other elongate flexible duct forms part of the disposable assembly.

Preferably the pump comprises an actuator which is driven by said motor, said fluid propulsion means being arranged to detachably engage the pump actuator.

Preferably said fluid propulsion means is arranged to magnetically couple with the pump actuator.

Preferably said fluid propulsion means comprises a piston.

Preferably the pump actuator comprises a reciprocating shaft having one end arranged to couple with said propulsion means.

Preferably the shaft reciprocates along an axis, said end of the shaft extending through an aperture in an outer wall of the pump body, the wall lying normal to said axis.

Preferably the pump comprises means for positioning the shaft in a position in which said end thereof is substantially in the same plane as the outer surface of said pump wall when stopped, so as to facilitate connection of the pump head.

Preferably the pump head is arranged to slide into a position on said outer surface of said pump wall in which said fluid propulsion means couples with the pump actuator.

Preferably the pump head is arranged to slidably rotate into a position on said outer surface of said pump wall in which said fluid propulsion means couples with the pump actuator.

Preferably the pump head is arranged to slidably rotate about an axis which extends normal to the plane of said outer surface of said pump wall, means being provided for rotationally coupling the pump head to the pump body for rotation about said axis.

Preferably the said means for rotationally coupling the pump head to the pump body comprises an electrical connector for coupling the cable to the pump body.

Preferably the electrical connector comprises a coaxial connector.

Preferably the pump head comprises one or more electrical terminals which engage corresponding electrical terminals on the pump body when the pump head is slid into said position on the pump body: these terminals may carry signals from a sensor in the head of the device.

Preferably means are provided for locking the pump head to the pump body when the motor is running.

Also in accordance with the present invention, as seen from a second aspect, there is provided a pump comprising pump body having a pump motor arranged to drive an actuator, and a pump head detachably mounted to the pump body and having a first port, a second port and fluid propulsion means for creating a flow of said fluid between said ports upon energisation of said pump motor, said pump head being arranged to sealingly contain said fluid.

Also in accordance with the present invention, as seen from a third aspect, there is provided a pump comprising pump body having a pump motor arranged to drive an actuator, and a pump head detachably mounted to the pump body and having fluid propulsion means for creating a flow of fluid between first and second ports of the pump head, the propulsion means being magnetically coupled to the pump actuator.

Also in accordance with the present invention, as seen from a third aspect, there is provided a motor having a body, a stator shaft fixed to the body and a rotor arranged to rotate around the shaft, the rotor having an axially extending circumferential formation on its external surface, means being provided on the body for engaging the formation to impart linear movement to an actuator upon rotation of the rotor.

Preferably the actuator comprises a reciprocating shaft which reciprocates along an axis, said axis extending parallel to the axis of motor rotation.

Preferably the actuator comprises an arm which extends radially from the shaft and engages the formation at the outer end thereof.

An embodiment of the present invention will now be described by way of an example only and with reference to the accompanying drawings, in which.

Figure 1:
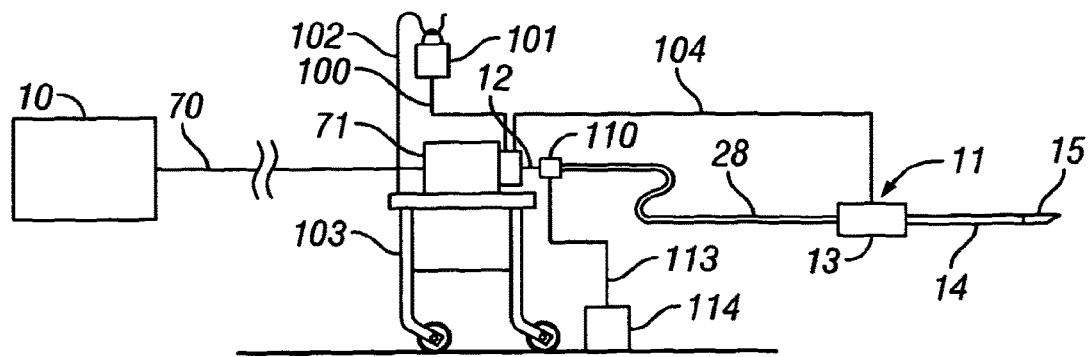
FIG. 1 is a schematic view of an embodiment of microwave applicator device in accordance with the present invention.

Referring to FIG. 1 of the drawings, there is shown a microwave applicator device comprising a microwave generator 10 having an elongate main output cable 70 connected to a pump 71. The cable 70 is directed connected inside the pump 71 to the proximal end of an elongate flexible feed cable 12. The distal end of the elongate flexible feed cable is connected to an applicator probe 11. The probe 11 comprises a handle portion 13 and an elongate shaft portion 14 extending from the handle 13. In use, the generator 10 generates a microwave signal which is transmitted along the cables 70,12 to the probe 11. The microwave signal is then transmitted along the shaft 14 of the probe to a radiating tip 15 at the distal end thereof.

Figure 2:
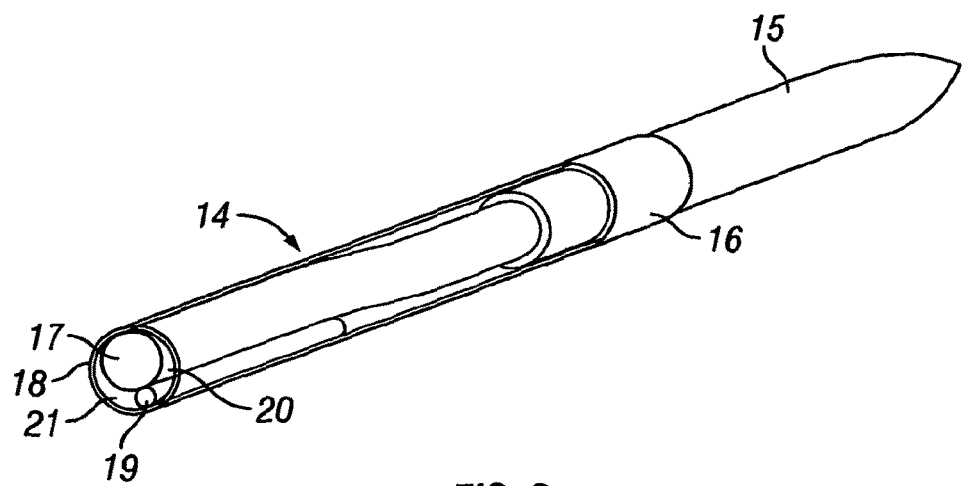
FIG. 2 is a perspective outline view of the distal end of a probe of the applicator device of FIG. 1.

Referring to FIG. 2 of the drawings, the shaft 14 comprises an external elongate tubular wall 14 formed of stainless steel. A co-axial transmission line 17 extends internally of the tubular wall 14, the transmission line 17 being coupled at its proximal end to the microwave feed cable 12 and at its distal end to a radiating antenna 16 which extends inside the tip 15 of the probe 11. An elongate flow dividing member 19, in the form of a solid cable or wire, co-extends with the co-axial transmission line 17 along a substantial part of the length thereof, the member 19 terminating a short distance away from the radiating antenna 16.

The combined diameter of the transmission line 17 and the flow dividing member 19 is slightly greater than the internal diameter of the tubular external wall 18, such that the transmission line 17 and flow dividing member both positively contact the internal surface of the external tubular wall 18 and each other along a substantial part of the length of the shaft 14. The transmission line 17 and flow dividing member 19 thus together define two flow channels 20, 21, which extend longitudinally of the shaft 14 from the proximal end to the point at which the flow dividing member 19 terminates. The two flow channels 20, 21 are interconnected beyond the point at which the flow dividing member 19 terminates.

Figure 3:
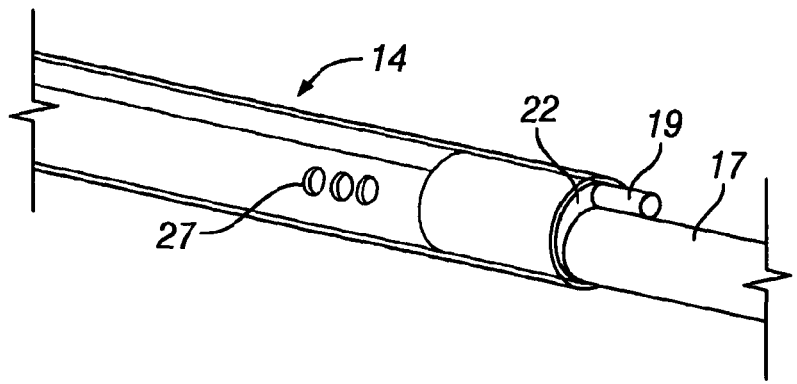
FIG. 3 is a perspective outline view of the proximal end of a shaft of the probe of the applicator device of FIG. 1.
Figure 4:
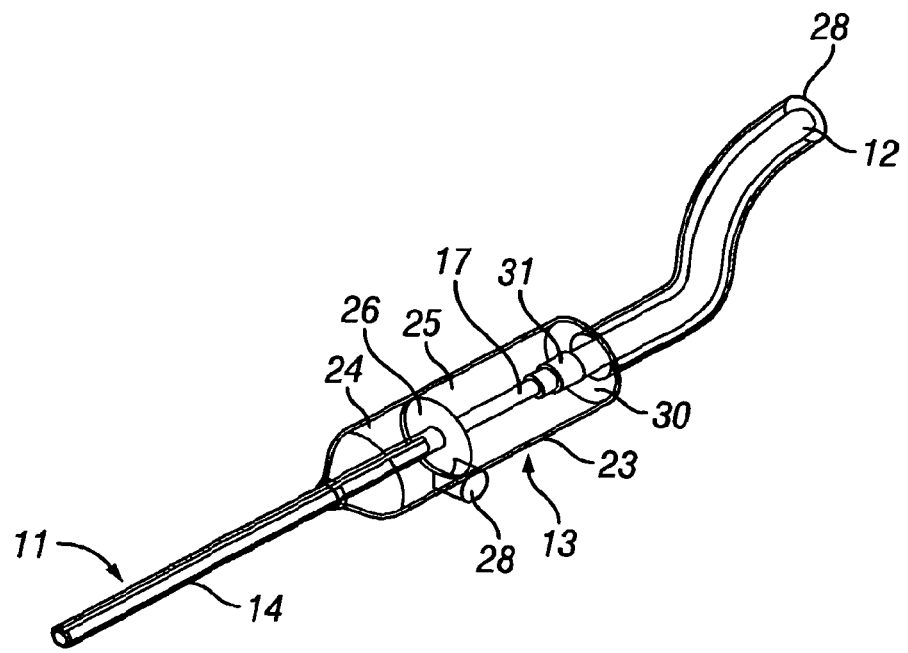
FIG. 4 is a perspective outline view of the proximal end of the probe and a microwave feed cable of the applicator device of FIG. 1.

Referring to FIGS. 3 and 4 of the drawings, one of the channels 20 is sealed by a member 22 at the proximal end of the shaft 14. A plurality of apertures 27 are formed in the external tubular wall 18 of the shaft 14 at the proximal end thereof, the apertures 27 communicating with the sealed channel 20. The proximal end of the shaft 14 extends into a manifold 23 disposed inside the handle 13 of the probe 11. The manifold 23 is generally cylindrical and is divided into two axially-disposed chambers 24, 25 by a boundary wall 26 which extends normal to the longitudinal axis of the shaft 14. The proximal end of the shaft 14 extends into the manifold 23 and through the boundary wall 26, such that the apertures 27 open into the distal chamber 24 of the manifold 23, the second (un-sealed) flow channel 21 of the shaft 14 opening into the proximal chamber 25 of the manifold 23. An inlet port 28 extends radially outwardly from the side wall of the manifold 23, the inlet port 28 communicating with the distal chamber 24 of the manifold 23.

The distal end of the feed cable 12 extends through the proximal end wall 30 of the manifold 23 and is connected to the proximal end of the transmission line 17. The feed cable 12 extends from the probe 11 towards the pump 71 inside a tube 28.

Figure 5:
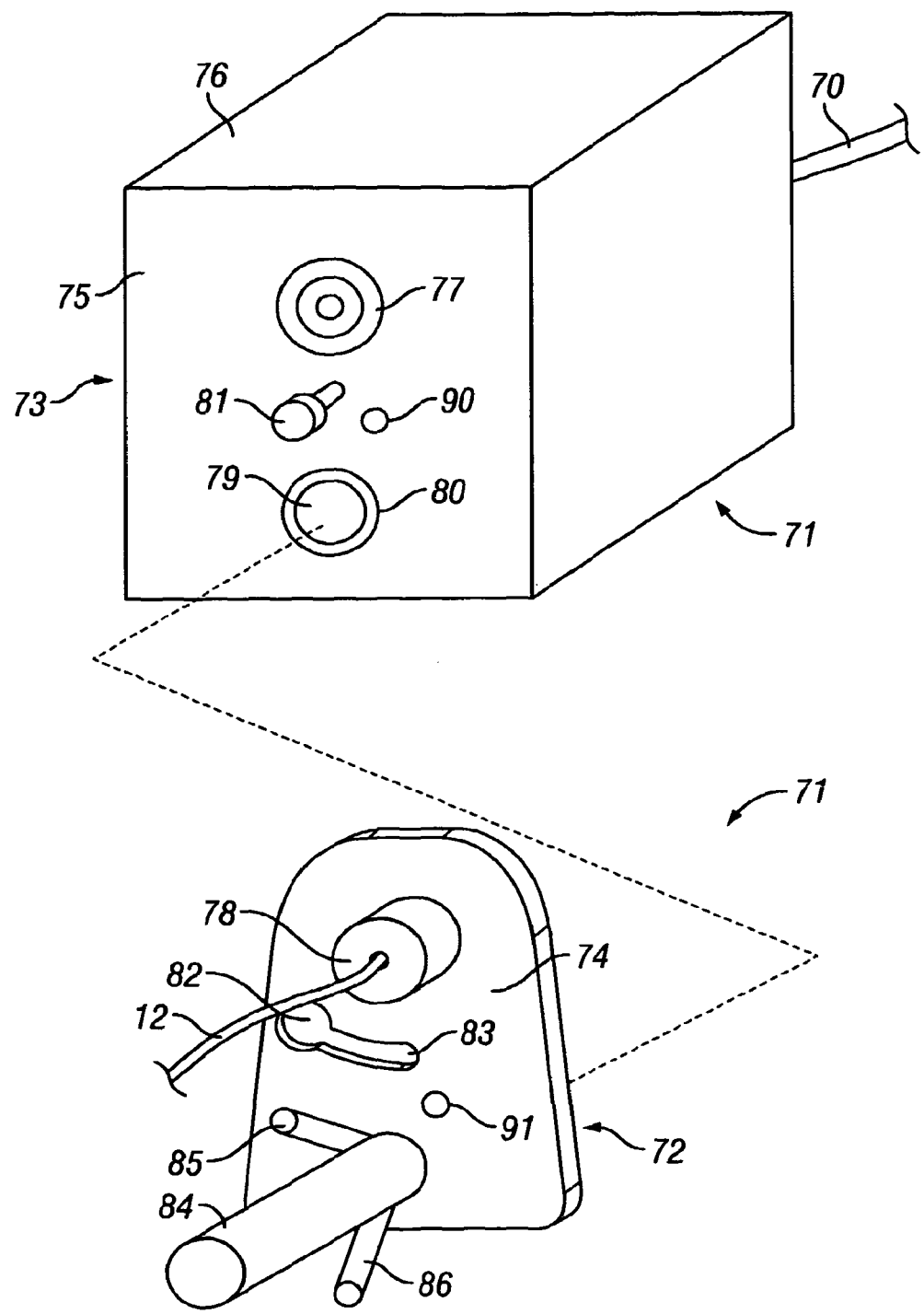
FIG. 5 is a perspective view of a pump of the applicator device of FIG. 1.

Referring to FIG. 5 of the drawings, the pump 71 comprises a pump head 72 detachably mounted to a pump body 73. The pump head 72 comprises a back plate 74 having a flat rear surface for fitting against the flat front surface 75 of a housing 76 of the pump body 73. The main microwave cable 70 from the microwave generator 10 is directly connected inside the pump housing 76 to a co-axial connector 77 disposed on the front wall 75 of the housing 76. The proximal end of the feed cable 12 extends into the back of a complimentary co-axial connector 78 disposed on the front surface of the back plate 74 of the pump head 72, the connector 78 having a co-axial terminals (not shown) which project rearwardly from the rear surface of the back plate 74 for engaging with the corresponding terminals of the connector 77 on the pump body 73.

A reciprocally-driven pump actuator shaft 79 of ferromagnetic material has an outer end which extends through an aperture 80 in the front wall 75 of the pump body 73. The aperture 80 is disposed radially outwardly of the connector 77. A T-shaped projection 81 having an enlarged outer end extends outwardly from the front wall 75 of the pump body 73 at a position that is disposed between the connector 77 and the aperture 80.

An aperture 82 is formed in the back plate 74 of the pump head 72, the aperture 82 having a diameter which is slightly greater than the diameter of the enlarged head of the T-shaped projection 81. A slot 82 extends across the back plate 74 from the aperture 82 in a counter clockwise direction, along an arcuate line which is centred about the centre of the co-axial connector 77.

An elongate tubular-walled pump barrel 84 extends outwardly from the front surface of the back plate 74 of the pump head 72, the pump barrel 84 being closed at its outer end by a hemispherical end wall. The inner end of the pump barrel 84 opens through an aperture in the back plate 74 of the pump head 72. Fluid inlet and outlet ports 85, 86 extend through the side wall of the pump barrel 84 at diametrically opposed positions adjacent the back plate 74.

In use, the rear surface of the back plate 74 of the pump head 72 is fitted in face-to-face registration with the front wall 75 of the pump body 73 by aligning the pump head 72 in front of the pump body 73, such that the connector 78 thereon is disposed in front of the connector 77 on the pump body 73 and such that the head of the T-shaped projection 81 is aligned with the aperture 82 in the back plate 74. The pump head 72 and the pump body 73 are then brought together, so that the connector 78 couples with the connector 77 and so that the head of the projection 81 extends through the aperture 82. Next, the pump head 72 is rotated in a clockwise direction, with the connector 77, 78 acting as the rotational axis for the pump head 72: the connector 77 is preferably free to rotate with respect to the pump body 73. Continued rotation of the pump head 72 causes the stem of the projection 81 to travel along the slot 83 in the back plate 74 until it reaches the end thereof: in this position the head of the projection 81 extends over the front surface of the back plate 74 and thereby locks the pump head 72 in-situ on the pump body 73 in a position where the proximal end of the pump barrel 84 is axially aligned with the aperture 80 in the front wall 75 of the pump body 73.

Figure 8:
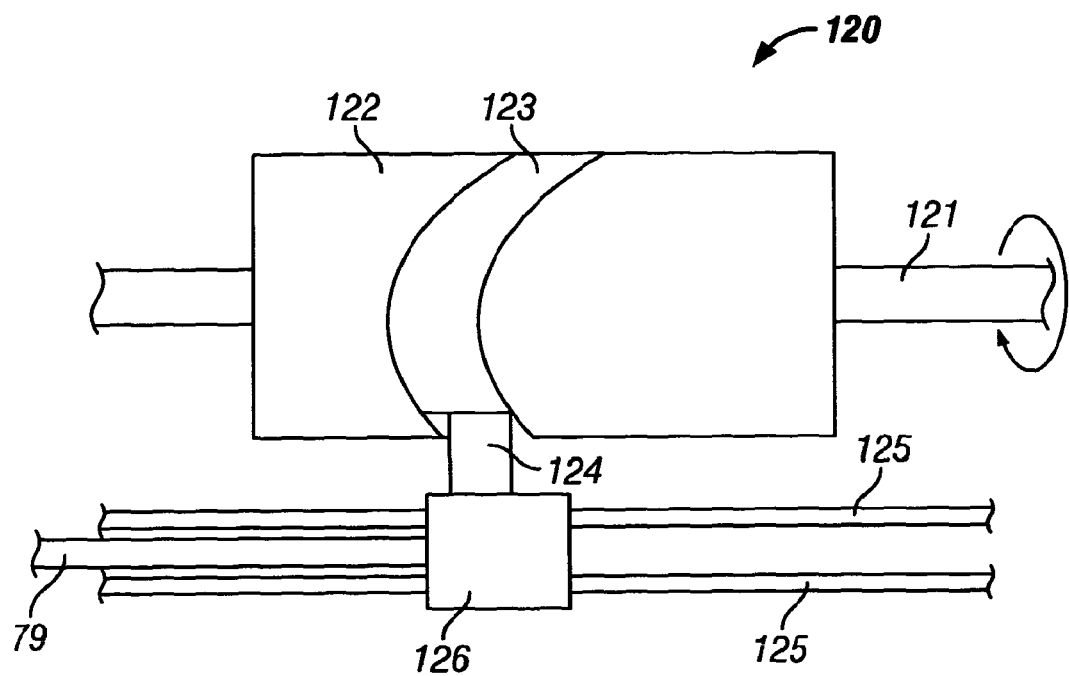
FIG. 8 is plan view of a motor and actuator of the pump of FIG. 5.

A pump motor is disposed inside the pump body 73, as shown in FIG. 8. When the motor is actuated, a pin 90 extends out of the front wall 75 of the pump body 73 into an aperture 91 formed in the back plate 74 of the pump head 72. In this manner, removal of the pump head 72 from the pump body 73 is prevented when the motor is running.

Figure 6:
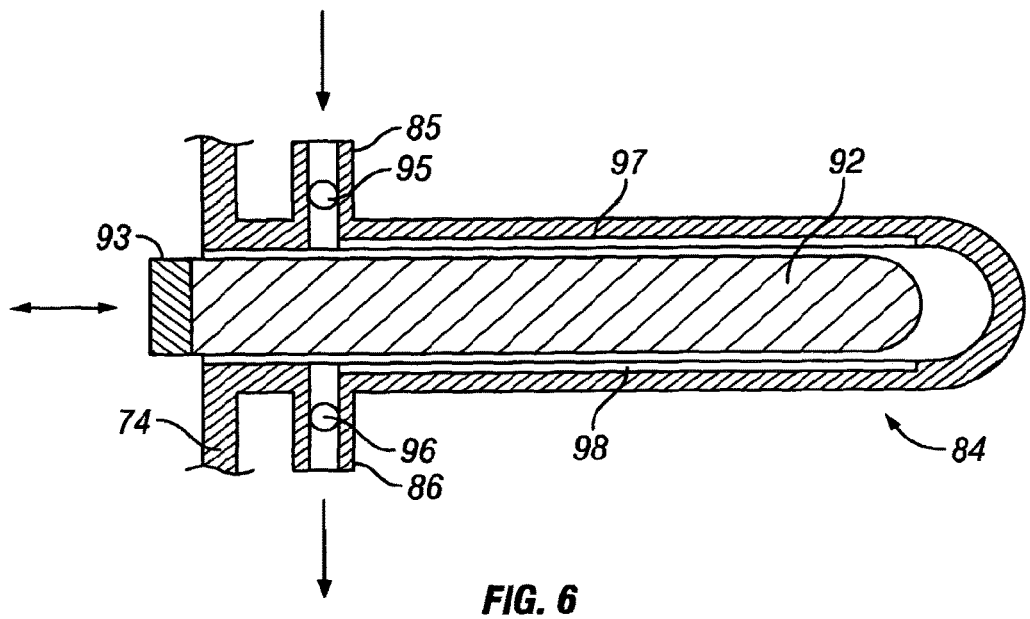
FIG. 6 is a sectional view through a portion of the head of the pump of FIG. 5.
Figure 7:
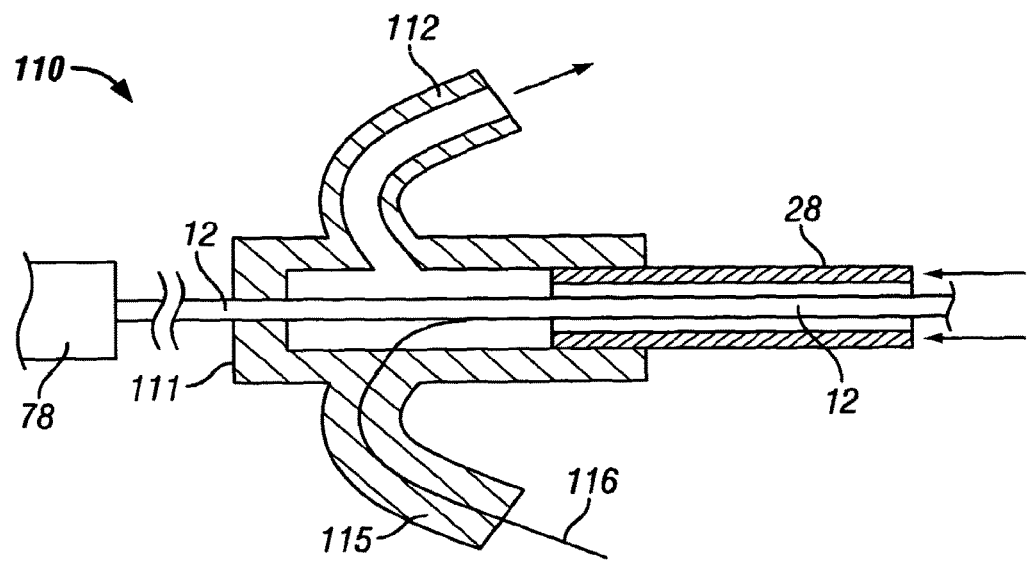
FIG. 7 is a sectional view through a manifold of the applicator device of FIG. 1.

Referring FIG. 6 of the drawings, a piston 92 is mounted inside the pump barrel 84 for reciprocal movement axially of the pump barrel 84. The proximal end of the piston 92 comprises a magnet 93, which magnetically couples to the end of the actuator shaft 79 disposed inside the aperture 80 in the front wall 75 of the pump body 73. The pump motor (FIG. 8) is controlled such that the axial end of the shaft 79 always lies co-planer with the front wall 75 of the pump body 73 when stopped, thereby ensuring that the pump head 72 can rotatably slide into position on the pump body 73 as hereinbefore described and ensuring that the magnet 73 satisfactorily couples with the shaft 79 once the locked position is reached.

The fluid inlet and outlet ports 85, 86 on the pump body 84 comprise respective valves 95, 96 which respectively allow fluid into and out of the pump barrel 84. The ports 85, 86 communicate with respective channels 97, 98 which extend axially along the internal surface of the tubular side wall of the pump valve 84 towards the distal end thereof.

In use is the shaft 79 of the pump actuator reciprocates, the piston 92 moves in and out of the pump barrel 84, thereby drawing fluid into the pump barrel 84 through the inlet 85 on the inward stroke and pumping fluid out of the pump barrel 84 through the outlet 86 on the outward stroke.

Referring again to FIG. 1 of the drawings, the inlet port 85 of the pump head 72 is connected via a tube 100 to a bag 101 of saline solution or other cooling fluid. The bag 101 may be suspended at an elevated position on an arm 102 extending upwardly from a trolley 103 in which the pump 71 is mounted. The outlet port 86 of the pump head 72 is connected via an elongate tube 104, which connects to the port 28 on the handle 13 of the probe (FIG. 4).

Referring again to FIGS. 2 to 4 of the drawings, when energised, the pump 71 pumps cooling fluid along the tube 104 into the distal chamber 24 of the manifold 23 of the probe 11 through the inlet port 28. The cooling fluid then flows through the apertures 27 in the external tubular wall 18 of the shaft 14 and into the flow channel 20. The cooling fluid then flows longitudinally of the shaft 14, thereby cooling the external wall 18 of the shaft and the transmission line 17. The cooling fluid then crosses from the flow channel 20 to the other flow channel 21 at the distal end of the shaft 14, beyond the point at which the flow dividing member 19 terminates. The cooling fluid then returns along the shaft 14 via the cooling channel 21, whereupon it flows into the proximal chamber 25 of the manifold 23. The fluid then flows out of the manifold 23 and into the tube 28, whereupon it flows over the cable 12 in an annular flow channel defined formed between the tube 28 and the co-axial cable 29.

The proximal end of the tube 28 is connected to a manifold 110 positioned adjacent the pump head 72. Manifold 110 comprises a first port 111, through which the cable 12 sealingly leaves the manifold 110 to enter the back of the connector 78 on the pump head 72. The manifold 110 comprises a second port 112, which fluidly connects to a tube 113 (FIG. 1) leading to a drain or collection vessel 114. One or more other ports 115 optionally allow other wires or cables 116 to sealingly enter the tube 28 and to co-extend with the cable 12 to the probe 11. These cables or wires 116 can carry signals from sensors, such as thermocouples mounted in the probe 11. Such sensors may disable the microwave generator 10 in the event that the probe 11 overheats.

The fluid from the bag 101 thus initially flows through the pump head 72 and along the tube 104 to the probe 11 where it cools the shaft 14 and transmission lines 17 of the probe. The fluid then returns via the tube 28 to cool the feed cable 12 before flowing to the drain or collection vessel 114.

Following use, the pump head can be disconnected from the pump body 73 by rotating it in a counter clockwise direction. The tube 100, the pump head 72, the tube 104, the probe 11, the tube 28, the cable 12, the manifold 110 and the tube 113 form a disposable sterile assembly which can be discarded following use to avoid any risk of cross-contamination and to avoid any necessity to clean any of the parts through which fluid flows. It will be appreciated that a disposable assembly can be provided as a relatively inexpensive item compared with the cost of the pump body 73.

Referring to FIG. 8 of the drawings, the pump body 73 comprises a pump motor 120 comprising a static shaft 121, which is mounted at its opposite ends to the pump housing 76. A tubular rota 122 extends around the shaft 121, means being provided between the shaft 121 and rota 122 for causing rotation of the latter about the shaft upon application of a suitable energisation signal.

The circumferential outer surface of the rota comprises a groove 123, which circumferentially and axially of the rota 123. A block 126 are slidably mounted on rails 125, which extend parallel to the motor shaft 121. A pin 124 projects from the block 126 into the grove, such that rotation of the rota 122 causes the block 126 to move to-and-fro along the rails 125. The aforementioned actuator shafts 79 of the motor extends from the block 126 into the aperture 80 in the front wall 75 of the pump body 73.

The grove 23 maybe sinusoidal, so that the actuator moves at the same rate in both directions. However, the groove 23 is preferably configured so that the inward stroke of the pump is short and so that the outward (pumping) stroke is long, thereby reducing intervals between successive fluid flows through the probe 11.

A microwave applicator probe in accordance with the present invention is relatively simple and inexpensive in construction, yet enables the probe to be reliably cooled.

The invention claimed is:

1. A method for delivering microwave energy to ablate tissue comprising:
    inserting an applicator into a tissue, the applicator comprising:
        an elongate shaft having a proximal end and a distal end, the elongate shaft comprising an external tubular wall, a transmission line and a flow dividing member, the transmission line and flow dividing member extending substantially the entire length of the external tubular wall, a first side of a transmission line outer wall and a first side of a flow dividing member outer wall contacting each other, a second side of the transmission line outer wall and a second side of the flow dividing member outer wall contacting an internal surface of the external tubular wall at two-spatially separated locations, defining a first cooling channel and a second cooling channel, the applicator further comprising a microwave antenna at a distal end of the applicator; and
        a handle connected to the proximal end of the elongate shaft, the handle comprising a manifold, the manifold comprising a distal chamber and a proximal chamber, the first cooling channel being in fluid communication with the distal chamber of the manifold and the second cooling chamber being in fluid communication with the proximal chamber of the manifold;
    activating a pump for pumping cooling fluid through the first cooling channel, the pump comprising a pump body, a pump head, and a first elongate flow duct extending between the pump and the first cooling channel, the pump having a power cable extending from the pump head to the applicator to power the microwave antenna;
    activating a microwave generator, the microwave generator generating a microwave signal, the signal to be transmitted to the microwave antenna of the applicator; and
    delivering microwave energy to the tissue to be treated.

2. The method of claim 1, wherein the first elongate flow duct is adjacent to the power cable.

3. The method of claim 1, further comprising a second elongate flow duct having a proximal end and a distal end, the distal end extending from the second cooling channel, the proximal end connected to the pump head, the second elongate flexible duct being arranged to carry the cooling fluid in the opposite direction of the first elongate flexible duct.

4. The method of claim 1, wherein the power cable is connected to the pump head by means of a connector provided on the pump head.

5. The method of claim 4, further comprising a second cable extending from the pump head to the microwave generator.

6. The method of claim 5, wherein the connector is capable of transferring electrical energy between the power cable and the second cable.

7. The method of claim 6, wherein the microwave power created in the generator is used to power the microwave antenna.

8. The method of claim 1, further comprising at least one aperture near the proximal end of the external tubular wall.

9. The method of claim 1, further comprising at least one aperture near the proximal end of the external tubular wall.

10. The method of claim 1, wherein the outer tubular wall further comprises a member, the member acting to seal the first cooling channel at the proximal end of the outer tubular wall and preventing cooling fluid from traveling proximally in the first cooling channel.

11. The method of claim 1, wherein the flow dividing member has a diameter equal to or greater than the difference between the internal diameter of the tubular external wall and the external diameter of said transmission line.

* * * * *